United States Patent [19]
Ortiz

[11] Patent Number: 6,096,030
[45] Date of Patent: Aug. 1, 2000

[54] LIGHT DELIVERY CATHETER AND PDT TREATMENT METHOD

[75] Inventor: Mark V. Ortiz, Santa Clara, Calif.

[73] Assignee: Pharmacyclics, Inc., Sunnyvale, Calif.

[21] Appl. No.: 08/935,412

[22] Filed: Sep. 23, 1997

[51] Int. Cl.⁷ .................................................... A61B 17/36
[52] U.S. Cl. ................. 606/14; 606/15; 607/92
[58] Field of Search .................... 606/7, 14–15; 604/96, 101; 607/88, 89

[56] References Cited

U.S. PATENT DOCUMENTS

| | | |
|---|---|---|
| 4,512,762 | 4/1985 | Spears . |
| 4,773,899 | 9/1988 | Spears ...................... 604/20 |
| 5,019,075 | 5/1991 | Spears et al. ................ 606/7 |
| 5,125,925 | 6/1992 | Lundahl ..................... 606/15 |
| 5,169,395 | 12/1992 | Narciso, Jr. . |
| 5,190,536 | 3/1993 | Wood et al. . |
| 5,196,005 | 3/1993 | Doiron et al. . |
| 5,219,346 | 6/1993 | Wagnières et al. . |
| 5,303,324 | 4/1994 | Lundahl . |
| 5,334,206 | 8/1994 | Daikuzono . |
| 5,370,608 | 12/1994 | Sahota et al. . |
| 5,431,647 | 7/1995 | Purcell, Jr. et al. . |
| 5,470,314 | 11/1995 | Walinsky . |
| 5,645,562 | 7/1997 | Haan et al. . |
| 5,709,653 | 1/1998 | Leone ....................... 604/20 |
| 5,770,243 | 12/1998 | Narciso, Jr. ................. 604/102 |
| 5,840,064 | 11/1998 | Liprie ........................ 604/96 |

FOREIGN PATENT DOCUMENTS

| | | |
|---|---|---|
| 0 411 132 A1 | 2/1991 | European Pat. Off. ......... A61N 5/06 |
| 0 649 637 | 4/1995 | European Pat. Off. . |
| 0 664 104 | 7/1995 | European Pat. Off. . |
| 93/18715 | 9/1993 | WIPO . |
| 96/07451 | 3/1996 | WIPO . |

*Primary Examiner*—Michael Peffley
*Assistant Examiner*—Roy Gibson
*Attorney, Agent, or Firm*—Townsend and Townsend and Crew LLP

[57] ABSTRACT

A light delivery catheter (2), for use in PDT treatments, includes a hollow sheath (4) with a balloon (24) at its distal end. Target tissue (33) at a target site on a hollow body organ, such as a blood vessel, is inoculated with an appropriate photosensitizing agent. A light guide (14) extends along the sheath and has a light-radiating portion or light source (20) at its end within the balloon. The balloon is positioned at the target site and target tissue is irradiated causing destruction of the target tissue. The balloon defines perfusion channels (30) when the balloon is inflated so that during use fluid can continue passing through the blood vessel. The light irradiating the vessel wall is preferably of generally equal intensity. This can be achieved in whole or in part in several different ways.

20 Claims, 3 Drawing Sheets

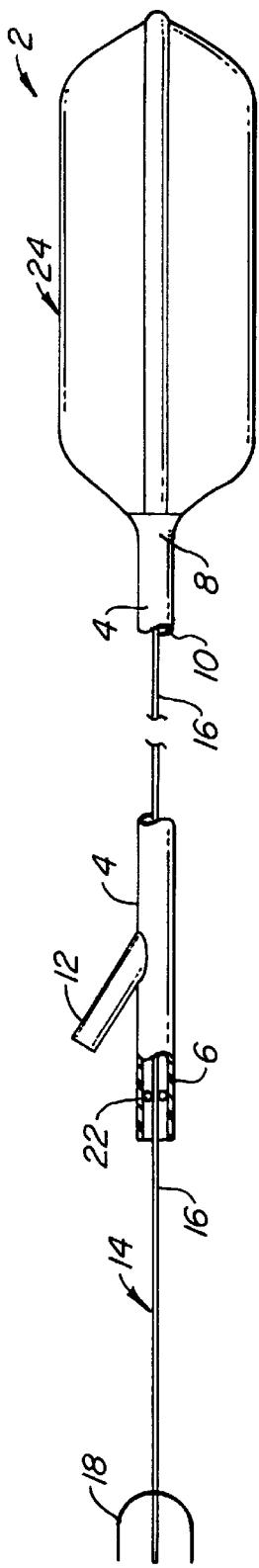
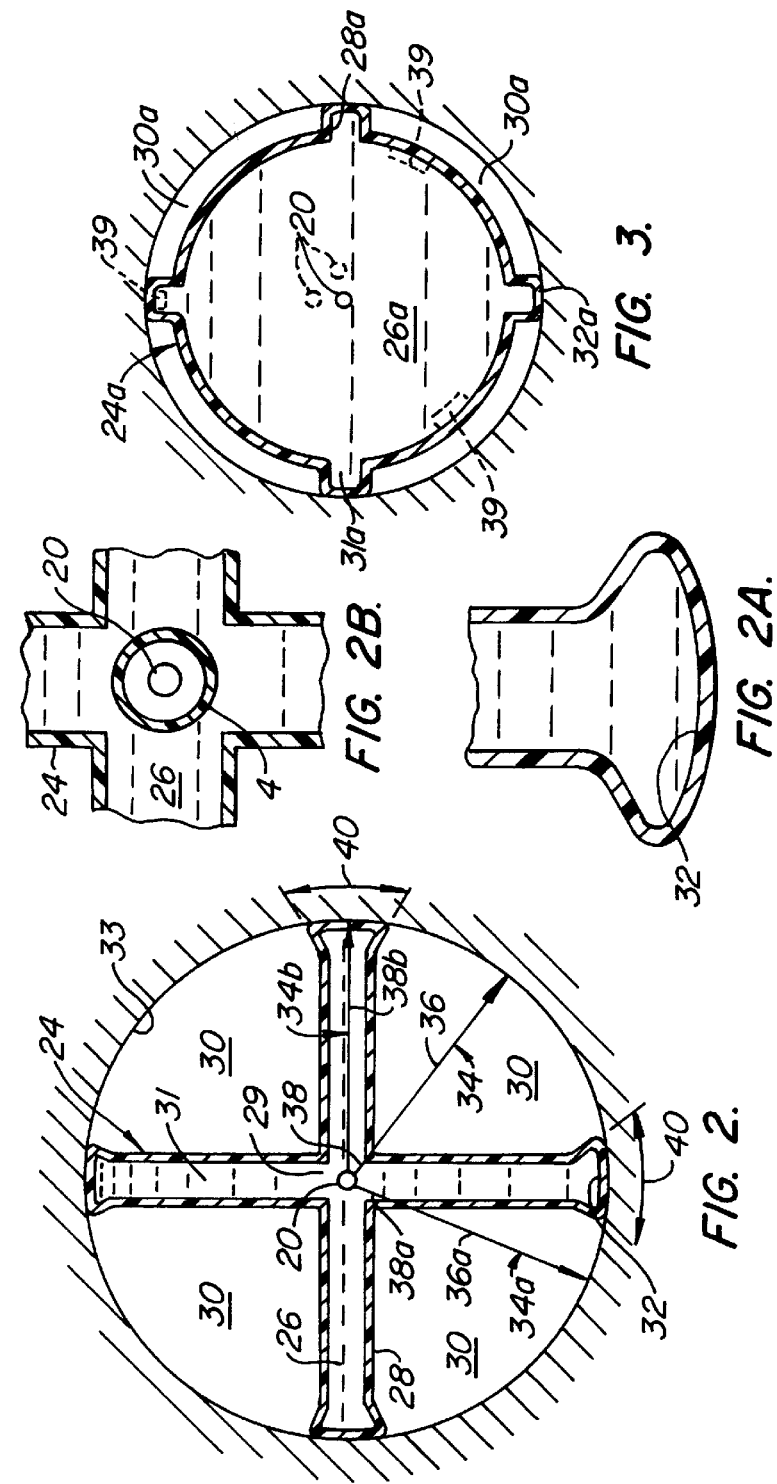

LIGHT DELIVERY CATHETER AND PDT TREATMENT METHOD

BACKGROUND OF THE INVENTION

It has been found that certain abnormal growths, such as certain cancerous tissue and atheromatous plaque, have an affinity for certain photosensitizing agents. Photosensitizing agents are compounds that, when exposed to light, or light of a particular wavelength or wavelengths, create $O_2$ radicals which react with the target cells. Examples of such agents include texaphyrins, hematoporphyrin, chlorins, and purpurins. In the case of living cells, such as cancer tumors, an appropriate photosensitizing agent is used to create the $O_2$ radicals which kill the target cells. In other situations, such as when it is desired to destroy atheromatous plaque tissue, an appropriate photosensitizing agent is activated to destroy the plaque by lysis (breaking up) of such plaque; mechanisms other than lysis may also be involved.

SUMMARY OF THE INVENTION

The present invention is directed to a light-delivery catheter and a photodynamic therapy (PDT) treatment method which uses a perfusion balloon to permit uninterrupted fluid flow through a hollow body organ, such as a blood vessel, the heart, bronchi, colon, esophagus, or urethra of a patient, while irradiating the walls of the organ. The intensity of the light irradiating the organ walls is preferably equalized using one or more techniques.

The light delivery catheter includes a sheath defining a lumen with a balloon mounted to the sheath in fluid communication with the lumen. A light guide is at least partially housed within the sheath and has a light-radiating portion (also called the light source) within the balloon. The sheath may or may not extend partly or fully within the balloon. The balloon defines one or more perfusion channels when the balloon is inflated so that fluid can continue passing through the organ housing the inflated balloon.

In use, the balloon is positioned within the hollow body organ. Depending on the particular therapy, target tissue may or may not be (but typically is) inoculated with an appropriate photosensitizing agent. The target tissue may or may not be a part of the hollow body organ. For example, the hollow body organ may be a section of artery and the target tissue may be the artery itself, tissue external of the artery or atheromateous plaque within the artery. The target tissue is irradiated, typically causing destruction of the target tissue as is desired. The light irradiating the organ wall is preferably of generally equal intensity. The light source can be a laser light source or other light source with suitable light characteristics.

Irradiation can be achieved in whole or in part in several different ways. The light irradiated from the light source, typically a cylindrical light diffuser, can be diffused so that it does not travel along mainly radially-directed paths. This diffusion can be accomplished by adding light-diffusing material into the normally light-transparent material of the balloon. The light source itself can be configured to radiate diffused light. Diffusion can also be provided by using a plurality of light sources within the balloon or adding light diffusing material within the fluid, typically a liquid, used to inflate the balloon. Also, the intensity of the irradiation of the vessel walls can be equalized by applying light-absorbing material to selected regions of the balloon, configuring the perfusion channels so each radial ray passes through equal lengths of perfusion channels, or otherwise equalizing the light attenuation along radially directed paths from the light source.

The size of the one or more perfusion channels can be selected according to the amount of perfusion desired for a particular patient for a particular procedure. This is typically dictated in a large part by the condition of the patient and the particular hollow body organ being treated. Also, for hollow body organs that are at different locations on the body, such as blood vessels, the location of the target site also affects the size of the perfusion channels.

A primary advantage of the invention is that PDT treatment methods can be carried out within a hollow body organ, typically a blood vessel, over a relatively extended period of time, such as one-half hour or longer, while permitting, for example, blood to continue passing through the organ. This permits the use of light at lesser intensities but over a longer period of time to be used to irradiate the inoculated target tissue to help prevent damage to adjacent healthy tissue. In addition, the provision of one or more perfusion channels provides fluid flow past the balloon during PDT treatment without the need to inflate and deflate the balloon in time with the beating heart. The perfusion channels also help to prevent patient discomfort and possible damage to, for example, limbs whose blood supply is cut off for too long a time.

The balloon inflation fluid can be a liquid or a gas. For example, in cardiovascular situations a liquid, such as sterile saline or sterile water, would typically be used, while in gastroenterology situations air or nitrogen can be used to inflate the balloon.

The fluid passing along the perfusion channels typically does not have the same light transmissive characteristics as either the balloon or the fluid that inflates the balloon. For example, when the hollow body organ is a blood vessel, blood tends to attenuate the intensity of the light much more than the balloon or the fluid within the balloon. Therefore, light rays that pass through a greater length of blood will strike the organ wall with a lower intensity than rays that pass through a lesser length of blood. The present invention recognizes this and contemplates the use of one or more methods or schemes (mentioned above) to help equalize the intensity of the light irradiating the organ wall, including diffusing the light, using light-absorbing material at selected regions on the balloon, and configuring the balloon so that the segments of radially directed light passing through the perfusion channels are of equal length.

The invention can find particular utility when there is a great selective uptake of the photosensitizing agent into the target tissue. Under this circumstance, the provision of highly equal light intensity irradiating the organ wall is not as critical as when the uptake of the photosensitizing agent is not as selective.

Other features and advantages of the invention will appear from the following description in which the preferred embodiments have been set forth in detail in conjunction with the company drawings.

BRIEF DESCRIPTION OF THE DRAWINGS

FIG. 1 is a simplified overall view of a catheter assembly made according to the invention;

FIG. 2 is an enlarged cross-sectional view of the inflated perfusion balloon of FIG. 1 within a blood vessel;

FIG. 2A illustrates an alternative embodiment of the distal end of one of the arms of the perfusion balloon of FIG. 2;

FIG. 2B illustrates an enlarged central portion of an alternative embodiment of the invention of FIG. 2 in which the sheath extends into the balloon to surround the cylindrical diffuser;

FIG. 3 is a view similar to that of FIG. 2, but of an alternative embodiment of the invention in which the perfusion channels are relatively small compared to the perfusion channels of the embodiment of FIG. 2;

DESCRIPTION OF THE PREFERRED EMBODIMENTS

Figure 4:
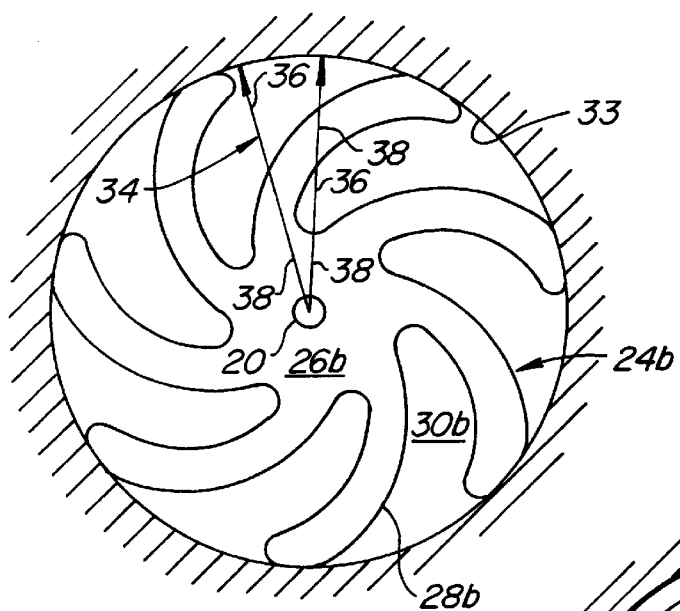
FIG. 4 illustrates a further embodiment of the invention in which the arms of the perfusion balloon extend radially and tangentially.

FIG. 1 illustrates a catheter assembly 2 comprising a sheath 4 having proximal and distal ends 6, 8. Sheath 4 is hollow and defines a central lumen 10 therein. Proximal end 6 has a Y-port 12 which fluidly communicates with central lumen 10. A light guide 14 includes an optical fiber 16 which extends along lumen 10. Optical fiber 16 terminates at its proximal end at a light receptor end 18 and at its distal end at a cylindrical diffuser 20 (see FIG. 2). Although not shown, a guidewire, for example, could also be used as a part of catheter assembly 2. A fluid seal 22 is used to provide a seal between optical fiber 16 and sheath 4 at proximal end 6.

A perfusion balloon 24 is mounted to distal end 8 of sheath 4. Balloon 24, see FIG. 2, has an x or + cross-sectional shape and defines a similarly-shaped balloon interior 26 therein. Balloon interior 26 is fluidly coupled to central lumen 10 so that interior 26 can be pressurized with an appropriate fluid, such as sterile saline or sterile water in the case of cardiovascular use. Sheath 4 may extend part way into or fully through interior 26 of balloon 24, see FIG. 2B, to surround part or all of diffuser 20. Sheath 4 may also extend all the way through interior 26 of balloon 24 and have a hole at its distal end to allow placement over a guidewire; inner space of sheath 4 would then be sealed from interior 26 of balloon 24 to allow inflation of the balloon.

Balloon 24 has a number of arms 28 which partially define perfusion channels 30. Therefore, balloon interior 26 includes a central region 29 housing diffuser 20 and several arm regions 31. Accordingly, when balloon 24 is inflated to its condition of FIG. 2, the distal ends 32 of arms 28 press against the vessel wall 33 of the blood vessel. As is shown in FIG. 2, cylindrical diffuser 20 (see FIG. 7A) is generally centrally placed within the blood vessel and within balloon 24. Conventional cylindrical diffusers 20 typically radiate light along radial paths, e.g. paths 34, 34a, 34b. Each radial path 34 has a perfusion segment 36 and a balloon interior segment 38 which together constitute radial transmission path 34. That is, segment 36 is that portion of path 34 that passes through perfusion channel 30 while segment 38 is that portion of path 34 that passes through balloon interior 26. Similarly, path 34a includes a perfusion segment 36a and a balloon interior segment 38a. However, path 34b does not pass through a perfusion channel 30 so that the entire path 34b is constituted by a balloon interior segment 38b.

Within a blood vessel, the fluid within perfusion channels 30 will be blood which attenuates the intensity of the light radiated from diffuser 20 to a much greater extent than the water or saline within balloon interior 26. Therefore, the intensity of the light beam passing along radial path 34 and striking vessel wall 33 will be of lesser magnitude than the intensity at vessel wall 33 along path 34a; the intensity at the end of path 34b will be the greatest of the three. To help counteract this difference in light intensity, portions or segments of balloon 24 are coated with a light-absorbing material, such as doped urethane (black) or other black-doped polymer balloon catheter materials. This may also be accomplished with other light-absorbing or light-reflecting materials. For example, the distal end 32 of arms 28 can be coated with a light-absorbing material as suggested by arrows 40. The amount of attenuation could be chosen to make the intensity of light along path 34b be the same as along path 34 (the greatest attenuation) or path 34a (an intermediate attenuation), or some other degree of attenuation. Light directed along paths between path 34 and path 34b could be attenuated in varying degrees such as by applying a variable thickness of the attenuating material along the length of each arm.

The size of perfusion channels 30 will depend primarily on the condition of the patient and the location of the treatment site of vessel wall 33. For example, when the hollow body organ being treated is an artery, an arterial treatment site within the leg can typically accommodate a greater reduction of blood flow than an arterial treatment site within the chest. It is usually preferred to make perfusion channels 30 as small as possible, consistent with the health of the patient, to reduce the attenuation created when the light passes through blood in the perfusion channels. FIG. 3 represents an extreme condition in which perfusion channels 30a are of a minimal size with arms 28a being rather short and stubby. In this case, the length the light travels through the blood within the perfusion channels 30a is short enough so the attenuation may not be sufficiently significant to require the provision of an attenuating material at the distal ends 32a of arms 28a.

FIG. 3 also illustrates an alternative construction in which one or more additional cylindrical diffusers 20, shown in dashed lines, are used. Because the diffusers are not collinear, the light from the diffusers will not be purely radially directed, but actually will cross one another. This type of diffusion of the light helps to reduce differences in the light intensity along vessel wall 33. FIG. 3 also illustrates, schematically in dashed lines, an optical feedback detector 39 mounted to balloon 24a to monitor light levels at different locations.

Other methods for diffusing light from the light source can also be used to help equalize the radiation intensity on vessel wall 33. For example, a light-diffusing material, such as soy bean emulsion sold by Pharmacia as Intralipid®, or other solutions of fatty light-scattering materials, can be incorporated into the fluid within balloon interior 26, 26a of balloon 24, 24a. Of course, the fluid and light-scattering materials must be safe in the event that balloon 24 ruptures or leaks. Balloon 24, 24a, which is preferably transparent to light of the desired wavelength, can have one or more light diffusing substances, such as aluminum oxide or zinc oxide, incorporated into the balloon material itself. Light diffusers sold by Physical Optics Corp. in both film and sheet form can also be used.

The distal ends 32 of arms 28 of the embodiments of FIGS. 2 and 3 exert radially-directed forces along relatively narrow regions of vessel wall 33. Distal ends 32 can be modified to an enlarged distal end 32a, as shown in FIG. 2A. This helps to increase the area pressing against vessel wall 33, thus reducing contact pressures. Another way to help maintain moderate contact pressures is by using arms 28b, see balloon 24b in FIG. 4, which are directed both radially and tangentially. When inflated, arms 28b do not press directly radially outwardly as in the embodiments of FIGS. 2 and 3, so as to reduce the force exerted against vessel wall 33. By appropriately selecting the size, shape, and number of arms 28b, the length of each of the balloon interior segments 38 can be made to be about equal. The radiation intensity on vessel wall 33 can be further equalized by the use of one or more methods to diffuse the light as discussed above.

Figure 5:
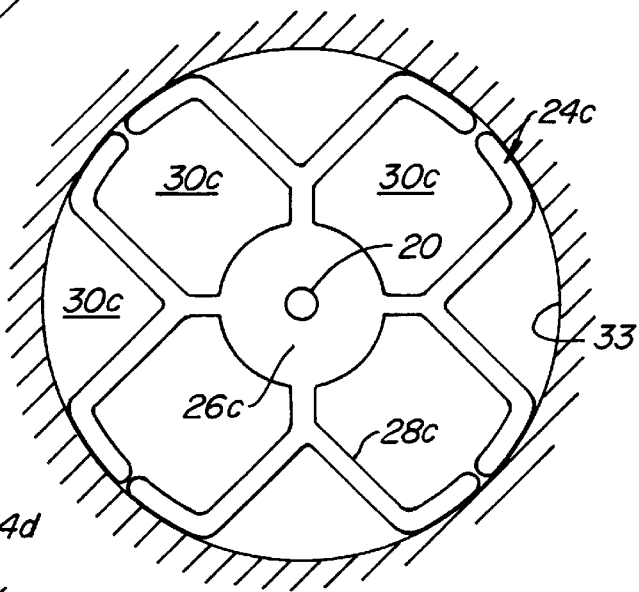
FIG. 5 illustrates another embodiment of the invention in which the arms of the perfusion balloon are generally Y-shaped.

FIG. 5 illustrates a further embodiment of the invention in which arms 28c are generally Y-shaped. This embodiment, as in the embodiment of FIG. 4, helps to equalize the distance each light ray passes through perfusion channels 30c and helps to reduce pressures on vessel wall 33 exerted by arms 28c.

Figure 6:
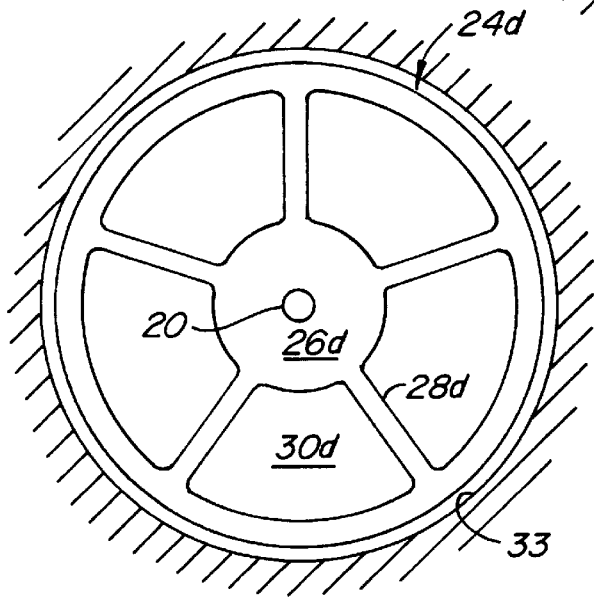
FIG. 6 illustrates a still further embodiment of the invention in which the balloon has a wagon wheel configuration.

FIG. 6 illustrates a further alternative embodiment of the invention similar to both FIGS. 2 and 5. However balloon 24d has five arms 28d instead of four arms and has the distal ends of the arms joined together to create a wagon wheel type of balloon catheter design.

Figure 7A:
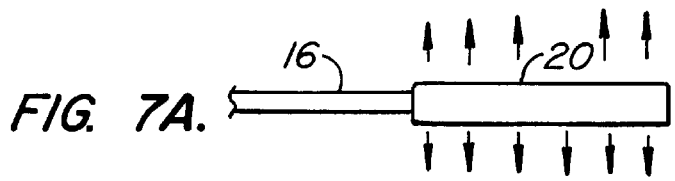
FIGS. 7A–7C illustrate a cylindrical diffuser, a spherical diffuser and a flat end diffuser, respectively.
Figure 7B:
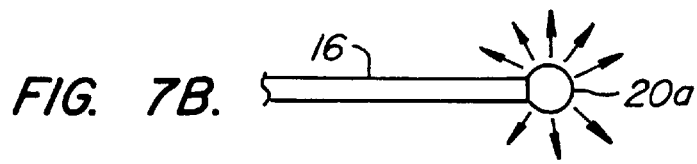
Figure 7C:
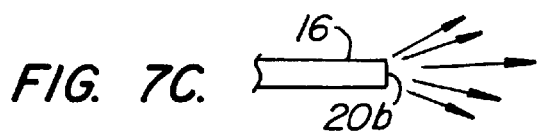

FIG. 7A, 7B, and 7C illustrate, schematically, three different types of light-radiating portions of light guide 14, typically light diffusers. FIG. 7A illustrates a cylindrical diffuser 20 such as that used in the embodiment of FIGS. 1–6. Various types of cylindrical diffusers are commercially available and are described in various issued patents. See, for example, U.S. Pat. No. 5,431,647, 5,196,005 and 5,303,324.

One or more spherical diffusers 20a, see FIG. 7B, can be used in lieu of cylindrical diffuser 20. While spherical diffusers 20a may not provide as uniform radiation as cylindrical diffusers within a generally tubular vessel, they are typically much less expensive.

FIG. 7C illustrates a diffuser 20b consisting essentially of the flat end of optical fiber 16. This type of diffuser is by far the simplest and cheapest of the three. Using light-diffusing materials within the fluid filling the balloon interior, together with other diffusion techniques, such a diffuser could be effective. With both spherical diffuser 20a and flat end diffuser 20b, a number of axially spaced-apart diffusers could be positioned along balloon interior 26 to aid irradiation uniformity.

Figure 8:
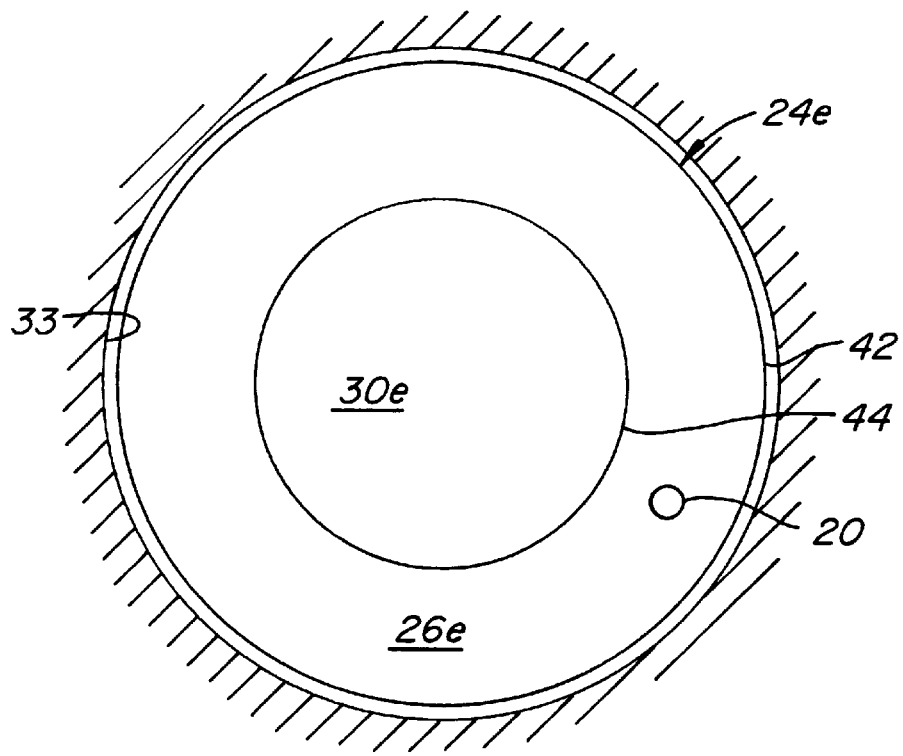
FIG. 8 illustrates an embodiment of the invention in which the balloon is in the form of a generally cylindrical sleeve.

FIG. 8 illustrates a generally cylindrical, sleeve-like perfusion balloon 24e having an outer wall 42 and an inner wall 44, the two walls defining an annular balloon interior 26e therebetween. A cylindrical diffuser 20 is located within balloon interior 26e. Perfusion channel 30e is defined within inner wall 44. To equalize the radiation intensity on vessel wall 33, several techniques may be used. Balloon interior 26e will typically be filled with a light-scattering media. Inner wall 44 will typically be coated with a light-reflective material. Light-scattering materials can also be incorporated into outer wall 42. It may be desirable to add a light-attenuating surface coating along portions of outer wall 42, such as adjacent to diffuser 20. Other irradiation intensity equalizing techniques may also be used.

Perfusion balloon 24e could be used as the basis for light therapy using a sleeve or cuff surrounding a body part such as a finger, a leg or an internal organ. Such a modified perfusion balloon 24e would not, of course, be part of a catheter. The modified perfusion balloon 24e could be formed into a tube or sleeve around the body part. In such case, the outer wall would be reflective.

In use, the target site, such as tissue adjacent to vessel wall 33, can be inoculated with a photosensitizing agent, such as hematoporphyrin, a texaphyrin, a purpurin or chlorin, by injecting the agent into the patient's bloodstream, by oral ingestion, by local application to the target tissue or by other appropriate means. Balloon 24 at the distal end 8 of sheath 4 is directed to a target site within a blood vessel in a conventional manner. Once in position, fluid is directed through Y-port 12, through central lumen 10 and into balloon interior 26 to inflate the balloon to the inflated condition shown in the figures. In the inflated condition, perfusion channels 30 are provided by the configuration of the balloon. The required cross-sectional area of the perfusion channels is determined largely by the state of the patient's health and the location of the treatment site. Once properly in place, light is directed through optical fiber 16 and to diffuser 20. Light radiates from diffuser 20 to irradiate vessel wall 33 in a generally uniform manner. Due to the provision of perfusion channels 30, balloon 24 can remain in place and inflated so that the PDT treatment can proceed for a relatively long period of time, such as thirty minutes or longer, without any substantial risk to the patient due to reduced (or interrupted) blood flow.

The term "light" has been used; light is to be considered in its broadest sense, encompassing all electromagnetic radiation. Light will typically be produced by arc lamps, LEDs or lasers at a certain frequency in the visible spectrum or near infrared for typical PDT treatments. Any and all patents, applications and publications referred to above are incorporated by reference.

Modifications and variations may be made to the disclosed embodiments without departing from the subject of the invention as defined by the following claims. For example, perfusion channels 30 could be used to permit fluids other than blood, such as bile or air, to bypass balloon 24. Also, if balloon 24 is used in an air passage, little or no effort may be needed to equalize irradiation intensity along the vessel wall; in this case perfusion channels 30 could be made as large as desired or possible because attenuation will not be affected to any substantial degree by the size of the perfusion passageway. Instead of multiple perfusion channels 30, a single perfusion channel could be used. Also, diffuser 20 could be located within a perfusion channel in appropriate cases, such as when air or some other non-light-attenuating fluid is the fluid passing through the perfusion channel. If desired, diffuser 20 could be an integral part of, as opposed to a separate component from, balloon 24.

What is claimed is:

1. A light delivery catheter comprising:
   a sheath defining a lumen:
   a balloon mounted to the sheath in fluid communication with the lumen;
   said balloon having a plurality of outwardly extending arms, said balloon at least partially defining at least one perfusion channel between said arms and a balloon interior when the balloon is inflated so that fluid can continue to pass through a hollow body organ when the balloon is inflated within the hollow body organ; and
   a light guide, said light guide having a light-radiating portion at least partially within the balloon so that light passing alone said light guide is radiated from said light-radiating portion into said balloon.

2. The catheter according to claim 1 wherein the light guide comprises an optical fiber.

3. The catheter according to claim 1 wherein the balloon further comprises at least one optical feedback detector for light level monitoring within the balloon.

4. The catheter according to claim 1 wherein the light radiating portion comprises a cylindrical light diffuser.

5. The catheter according to claim 4 wherein the cylindrical light diffuser is a separate component from the balloon.

6. The catheter according to claim 1 wherein the light-radiating portion of said light guide is fully housed within the balloon interior.

7. The catheter according to claim 1 wherein the light guide comprises a plurality of light-radiating portions.

8. The catheter according to claim 1 wherein said balloon interior comprises a central region and a plurality of arm regions, said arm regions defined by said arms.

9. The catheter according to claim 1 wherein said arms extend radially and tangentially outwardly.

10. The catheter according to claim 1 wherein said arms extend radially outwardly.

11. The catheter according to claim 1 wherein at least one said arm has a generally Y-cross-sectional shape.

12. The catheter according to claim 1 wherein said arms have enlarged, pressure-reducing distal ends.

13. The catheter according to claim 1 wherein said light guide is housed within said lumen.

14. The catheter according to claim 1 wherein the balloon comprises light-diffusing material to diffuse light from said light-radiating portion passing through said light-diffusing material.

15. The catheter according to claim 1 further comprising means for equalizing radiation intensity from the balloon.

16. The catheter according to 1 further comprising light diffusing material as a part of the balloon.

17. The catheter according to claim 1 further comprising a plurality of said light-radiating portions which helps to equalize radiation intensity from the balloon.

18. The catheter according to 1 further comprising a light-diffusing material within a fluid within the balloon interior which helps to equalize radiation intensity from the balloon.

19. A light delivery catheter comprising:

a sheath defining a lumen;

a balloon mounted to the sheath in fluid communication with the lumen;

said balloon defining at least one perfusion channel and a balloon interior when the balloon is inflated so that fluid can continue to pass through a hollow body organ when the balloon is inflated within the hollow body organ;

a light guide, said light guide having a light-radiating portion at least partially within the balloon so that light passing along said light guide is radiated from said light-radiating portion into said balloon; and radiation-absorbing material along selected sections of the balloon which equalizes radiation intensity from the balloon.

20. A light delivery catheter comprising:

a sheath defining a lumen;

a balloon mounted to the sheath in fluid communication with the lumen;

said balloon defining at least one perfusion channel and a balloon interior when the balloon is inflated so that fluid can continue to pass through a hollow body organ when the balloon is inflated within the hollow body organ;

a light guide, said light guide having a light-radiating portion at least partially within the balloon so that light passing alone said light guide is radiated from said light-radiating portion into said balloon;

said balloon having radially outwardly-extending arms at least partially defining said at least one perfusion channel, said arms having distal ends; and radiation-absorbing material at said distal ends of said arms which equalizes radiation intensity from the balloon.

* * * * *